United States Patent
Schattenmann

(12) 
(10) Patent No.: US 6,384,258 B1
(45) Date of Patent: May 7, 2002

(54) METHOD FOR MAKING ORGANYLORGANOOXYSILANES

(75) Inventor: Florian Johannes Schattenmann, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/850,959

(22) Filed: May 9, 2001

(51) Int. Cl.[7] .................................................. C07F 7/08
(52) U.S. Cl. ...................................................... 556/481
(58) Field of Search .......................................... 556/481

(56) References Cited

U.S. PATENT DOCUMENTS 2,380,995 A    8/1945   Rochow

OTHER PUBLICATIONS

Bazant et al., "Organosilicon Compounds", vol. 2, part 1, Academic Press, N.Y., 1965, pp. 109 and 307.*

"The Addition of Silicon Hydrides to Olefinic Double Bonds, Part II. The Use of Group VIII Metal Catalysts", by J.L. Speier, J.A. Webster and Garrett H. Barnes, Feb. 20, 1957, pps. 974–979.

"Some Tetrasubstituted Naphtyl–and Tolyslsilanes" by H. Gilman, C.G. Brannen and R.K. Ingham, Jul. 20, 1955, pp. 3916–3919.

* cited by examiner

*Primary Examiner*—Paul F. Shaver
(74) *Attorney, Agent, or Firm*—Bernadette M. Bennett; Noreen C. Johnson

(57) ABSTRACT

A method for the preparation of organylorganooxysilanes containing at least one silicon-carbon bond is provided comprising reacting at least one triorganooxysilane with at least one base.

15 Claims, No Drawings

METHOD FOR MAKING ORGANYLORGANOOXYSILANES

STATEMENT REGARDING FEDERALLY SPONSORED RESEARCH AND DEVELOPMENT

The government may have certain rights in this invention pursuant to contract number DE-FC02-98CH10931 awarded by the United States Department of Energy.

BACKGROUND OF THE INVENTION

The present invention relates to a method for making organylorganooxysilanes. More particularly, the present invention relates to a process involving the reaction of a triorganooxysilane in the presence of a base.

Organylorganooxysilanes are silicon-containing compounds of the formula $R_mSi(RO)_n$ where each R independently represents a monovalent hydrocarbon group such as an alkyl group, aryl group, aralkyl groups, alkaryl groups, cycloalkyl groups, or bicycloalkyl groups; "n" is in a range between 1 and 3; "m" is in a range between 1 and 3; and "n+m" is 4. Silicon-containing compounds with silicon-carbon bonds, such as organylorganooxysilanes, are commonly made from silicon dioxide via elemental silicon or from a compound containing a silicon-hydrogen bond.

Rochow et al., U.S. Pat. No. 2,380,995 first described the process commonly used commercially for the production of silicon-containing compounds with a silicon-carbon bond. The Rochow process uses silicon, also referred to as elemental silicon, as a starting material. To prepare elemental silicon, silicon dioxide must be reduced. The elemental silicon is then oxidized to yield a silicon-carbon bond via a reaction of the silicon with methyl chloride in the presence of a copper catalyst. The silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicon-carbon bonds from silicon dioxide using the Rochow process is expensive and not energy efficient.

Silicon-hydrogen bonds are also a useful starting material for formation of silicon-carbon bonds. Gilman et al., *J. Am. Chem. Soc.* 1955, 77, 3916, discuss the use of organometallic reagents to produce a silicon-carbon bond from a silicon compound containing a silicon-hydrogen bond. The most prevalent disadvantage of the use of organometallic reagents is the impracticality and the high price of the reagents.

Speier et al., *J. Am. Chem. Soc.* 1957, 79, 974, discuss the process known as hydrosilylation. Hydrosilylation involves the catalyzed addition of a silicon-hydrogen bond across a π-bond, typically an alkene or alkyne, to form a silicon-carbon bond. Typically, the bulk of commercially manufactured silicones only have methyl groups, one-carbon fragments, connected to the silicon atoms. Unfortunately, it is impossible to connect a one-carbon fragment directly to the silicon atom with the use of an alkene or alkyne.

In the past, the synthesis of silicon-containing compounds with silicon-carbon bonds has relied heavily on the reduction of silicon dioxide to elemental silicon or the use of a compound containing a silicon-hydrogen bond. Unfortunately, the large amount of energy needed for synthesizing silicones such as organylorganooxysilanes from silicon dioxide can be problematic. Additionally, there is no efficient pathway from silicon-hydrogen to silicon-carbon bonds known that allows connection of one-carbon fragments to the silicon atom. Thus, new synthetic routes are constantly being sought which can form silicon-carbon bonds from silicon-hydrogen bonds.

SUMMARY OF THE INVENTION

The present invention provides a method for the preparation of organylorganooxysilanes containing at least one silicon-carbon bond comprising reacting at least one triorganooxysilane with at least one base.

DETAILED DESCRIPTION OF THE INVENTION

The present invention relates to a process involving the reaction of at least one triorganooxysilane and at least one base to form an organylorganooxysilane containing at least one silicon-carbon bond. Triorganooxysilanes are of the formula $(RO)_3SiH$ where each R independently represents a monovalent hydrocarbon group such as alkyl groups, aryl groups, aralkyl groups, alkaryl groups, cycloalkyl groups, or bicycloalkyl groups. The term "alkyl group" is intended to designate both normal alkyl and branched alkyl groups. Normal and branched alkyl groups are preferably those containing carbon atoms in a range between about 1 and about 22, and include as illustrative non-limiting examples methyl, ethyl, propyl, isopropyl, butyl, tertiary-butyl, pentyl, neopentyl, hexyl, octyl, decyl, dodecyl. Aryl groups include an example such as phenyl. Cyclo- or bicycloalkyl groups represented are preferably those containing ring carbon atoms in a range between about 3 and about 12 with a total number of carbon atoms less than or equal to about 50. Some illustrative non-limiting examples of cycloalkyl groups include cyclobutyl, cyclopentyl, cyclohexyl, methylcyclohexyl, and cycloheptyl. Preferred aralkyl groups are those containing carbon atoms in a range between about 7 and about 14; these include, but are not limited to, benzyl, phenylbutyl, phenylpropyl, and phenylethyl. Typical triorganooxysilanes include trialkoxysilanes such as trimethoxysilane, and triethoxysilane; triaryloxysilanes such as triphenoxysilane; as well as tri(alkoxyaryloxy)silanes such as dimethoxyphenoxysilane. Typically, the level of purity of the triorganooxysilane is at least about 80% by weight and preferably, about 95% by weight.

Bases include, but are not limited to, sodium methoxide ($NaOCH_3$), sodium hydride (NaH), potassium-tert-butoxide [K—O—t—$(CH_2)_3CH_3$], and combinations thereof. The base is preferably sodium methoxide. Bases also include metal hydroxides, metal amides, metal alkoxides, and metal aryloxides.

Organylorganooxysilanes are compounds of the formula $R_mSi(RO)_n$ where R is defined as above, "n" is in a range between 1 and 3, "m" is in a range between 1 and 3, and "n+m" is 4. Preferably, R is methyl or ethyl, m is 1 and n is 3.

The reaction commonly can be practiced in a fixed bed reactor. The method for preparation of organylorganooxysilanes, however, can be performed in other types of reactors, such as fluidized bed reactors and stirred bed reactors. More specifically, the fixed bed reactor is a column that contains the base wherein a carrier gas, such as an inert gas of hydrogen or argon, is passed through at a rate in a range between about 0.1 milliliters per minute (ml/min) and about 100 ml/min and preferably, in a range between about 0.5 ml/min and about 30 ml/min. The triorganooxysilane is typically fed into the carrier gas stream. A stirred bed is similar to a fixed bed in which there is mechanical agitation of some sort in order to keep the bed in constant motion. A fluidized bed reactor, on the other hand, is a bed comprising base which is fluidized; that is, the base is suspended in the gas, typically argon, that is passed through the reactor. Reaction typically occurs at a temperature in a range between about 50° C. and about 600° C. and commonly, in a range between about 200° C. and about 450° C.

The reaction of the present invention can be performed in batch mode, continuous mode, or semi-continuous mode. With a batch mode reaction, for instance, all of the reactant components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants.

The triorganooxysilane is typically added to the reactor via any convenient method to provide batch, continuous, or semi-continuous means of addition. A pumping device, such as a motor driven syringe, is an example of a continuous means of addition. A motor driven syringe allows for consistent amounts of triorganooxysilane to be added to the reaction mixture at given time intervals. Addition of the triorganooxysilane via a motor driven syringe is illustrative and non-limiting. Manual injection is also a common method for the addition of triorganooxysilanes. Typically, the triorganooxysilane is added at a rate in a range between about 0.1 milliliters per hour (ml/h) and about 10 ml/h, and preferably, in a range between about 0.5 ml/h and about 2.5 ml/h. The triorganooxysilane is typically added in a mole ratio of base to triorganooxysilane in a range between about 10:1 and about 1:100 and commonly, a mole ratio of base to triorganooxysilane in a range between about 5:1 and 1:10. The reaction is typically carried out at about atmospheric pressure.

Products in the organylorganooxysilane synthesis may be isolated by any convenient means. Typically, product(s) may be isolated by condensation into fractions typically referred to as condensate. Products may be purified by any convenient means such as distillation. Once the fractions are collected, the formation of the organylorganooxysilane may be confirmed by such methods as gas chromatography (GC), gas chromatography-mass spectroscopy (GC/MS), and proton nuclear magnetic resonance spectroscopy ($^1$H-NMR), carbon nuclear magnetic resonance spectroscopy ($^{13}$C-NMR) and silicon nuclear magnetic resonance spectroscopy ($^{29}$Si-NMR).

Organylorganooxysilanes obtained by the present method may be used in a wide variety of applications. For example, organylorganooxysilanes may be used as precursors to silicones and organofunctional silicon compounds, precursors to pure and ultra-pure silicon dioxide, coupling agents, additives for plastic applications, and adhesion promoters.

In order that those skilled in the art will be better able to practice the invention, the following examples are given by way of illustration and not by way of limitation.

EXAMPLE 1

Sodium methoxide [1.0 grams (g); 18.5 millimole (mmol)] was charged into a fixed-bed flow reactor with vertical furnace at room temperature and flushed with argon carrier gas at a rate of 5 milliliters per minute (mL/min). The reactor was heated in the presence of argon as carrier gas to a temperature of 150° C. Trimethoxyliane [1.72 milliliters per hour (mL/h); 13.5 millimoles per hour (mmol/h); 10 milliliters(mL) total] was fed into the carrier gas stream using a motor driven syringe. The reactor effluent downstream was collected in fractions using a water-chilled condenser and methyltrimethoxysilane [MeSi(OMe)$_3$] formation was confirmed by gas chromatography and gas chromatography/mass spectroscopy. The reaction was carried out with a temperature ramp. After collecting a fraction, typically in a range between about 0.5 grams and about 2 grams, the reactor temperature was increased by 25° C. as indicated in Table 1. The temperature was ramped for screening purposes. The percentages of methyltrimethoxysilane refer to percentages of the individual samples downstream of the reactor including unreacted trimethoxysilane. Results can be seen in Table 1.

TABLE 1

| Fraction | Weight of sample (g) | Temperature (° C.) | % MeSi(OMe)$_3$ |
|---|---|---|---|
| 1 | 0.51 | 150 | 0 |
| 2 | 0.93 | 175 | 0 |
| 3 | 1.25 | 200 | 2.9 |
| 4 | 0.95 | 225 | 2.6 |
| 5 | 0.81 | 250 | 3.7 |
| 6 | 1.35 | 275 | 9.9 |
| 7 | 0.92 | 300 | 13.1 |
| 8 | 0.80 | 325 | 10.4 |

EXAMPLE 2

The procedure of Example 1 was followed with the following modifications: reaction was carried out at a fixed temperature of 325° C. Results can be seen in Table 2.

TABLE 2

| Fraction | Weight of sample (g) | Temperature (° C.) | % MeSi(OMe)$_3$ |
|---|---|---|---|
| 1 | 1.22 | 325 | 15.8 |
| 2 | 1.00 | 325 | 16.3 |
| 3 | 0.85 | 325 | 14.0 |
| 4 | 0.97 | 325 | 1.2 |
| 5 | 1.33 | 325 | 0.5 |
| 6 | 1.15 | 325 | 0.0 |
| 7 | 0.62 | 325 | 0.0 |

EXAMPLE 3

The procedure of Example 1 was followed with the following modifications: sodium hydride (1.01 g; 42.1 mmol) was the base used instead of sodium methoxide; trimethoxysilane (2.13 mL/h; 16.7 mmol/h, 12 mL total); carrier gas=argon (14.4 mL/min). Reaction was carried out with a temperature ramp. After collecting a fraction, the reactor temperature was increased by 25° C. as indicated in Table 3. Results can be seen in Table 3.

TABLE 3

| Fraction | Weight of sample (g) | Temperature (° C.) | % MeSi(OMe)$_3$ |
|---|---|---|---|
| 1 | 0.93 | 200 | 0.5 |
| 2 | 0.84 | 225 | 2.8 |
| 3 | 0.95 | 250 | 7.9 |

TABLE 3-continued

| Fraction | Weight of sample (g) | Temperature (° C.) | % MeSi(OMe)$_3$ |
|---|---|---|---|
| 4 | 1.01 | 275 | 9.8 |
| 5 | 0.76 | 300 | 15.9 |
| 6 | 0.64 | 325 | 37.3 |

EXAMPLE 4

The procedure in Example 1 was used with the following modifications: potassium-tert-butoxide (0.98 g; 8.7 mmol) was the base used instead of sodium methoxide; trimethoxysilane (2.13 mL/h; 16.7 mmol/h); carrier gas=argon (75 mL/min). Reaction was carried out with a temperature ramp. After collecting a fraction, the reactor temperature was increased by 25° C. Results can be seen in Table 4.

TABLE 4

| Fraction | Weight of sample (g) | Temperature (° C.) | % MeSi(OMe)$_3$ |
|---|---|---|---|
| 1 | 1.60 | 150 | 0.0 |
| 2 | 0.87 | 175 | 1.8 |
| 3 | 0.84 | 200 | 3.5 |
| 4 | 1.58 | 225 | 1.5 |
| 5 | 1.67 | 250 | 0.7 |

EXAMPLE 5

The procedure in Example 1 was used with the following modifications: sodium hydride (1.00 g; 41.7 mmol) was used instead of sodium methoxide; triethoxysilane (1.5 mL/h; 8.1 mmol/h) was used instead of trimethoxysilane; carrier gas= argon (5 mL/min). Reaction was carried out with a temperature ramp. After collecting a fraction, the reactor temperature was increased by 25° C. The percentages of ethyltriethoxysilane [EtSi(OEt)$_3$] refer to percentages of the individual samples downstream of the reactor including unreacted trimethoxysilane. Results can be seen in Table 5.

TABLE 5

| Fraction | Weight of Sample (g) | Temperature (° C.) | % EtSi(OEt)$_3$ |
|---|---|---|---|
| 1 | 1.03 | 200 | 0.0 |
| 2 | 1.20 | 225 | 0.0 |
| 3 | 0.99 | 250 | 0.6 |
| 4 | 0.98 | 275 | 6.1 |

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method for the preparation of organylorganooxysilanes containing at least one silicon-carbon bond comprising reacting at least one triorganooxysilane with at least one base.

2. The method according to claim 1, wherein the triorganooxysilane comprises trialkoxysilanes, triaryloxysilanes, tri(alkoxyaryloxy)silanes, or combinations thereof.

3. The method according to claim 2, wherein the triorganooxysilane comprises trimethoxysilane.

4. The method according to claim 2, wherein the triorganooxysilane comprises triethoxysilane.

5. The method according to claim 1, wherein the base comprises sodium methoxide, sodium hydride, potassium-tert-butoxide, or combinations thereof.

6. The method according to claim 5, wherein the base comprises sodium methoxide.

7. The method according to claim 1, wherein the reaction occurs in a reactor bed comprising a fixed bed reactor, a fluidized bed reactor, or a stirred bed reactor.

8. The method according to claim 7, wherein the reaction is operated in batch mode.

9. The method according to claim 7, wherein the reaction is operated in continuous mode.

10. The method according to claim 1, wherein the reaction is conducted at a temperature in the range between about 50° C. and about 600° C.

11. The method according to claim 10, wherein the reaction is conducted at a temperature in a range between about 200° C. and about 450° C.

12. The method according to claim 1, wherein the base is present in a mole ratio of base to triorganooxysilane in a range between about 10:1 and about 1:100.

13. The method according to claim 12, wherein the base is present in a mole ratio of base to triorganooxysilane in a range between about 5:1 and about 1:10.

14. A method for the preparation of methyltrimethoxysilane comprising reacting trimethoxysilane with sodium methoxide wherein the sodium methoxide is present in a mole ratio of sodium methoxide to trimethoxysilane in a range between about 5:1 and about 1:10.

15. A method for the preparation of ethyltriethoxysilane comprising reacting triethoxysilane with sodium hydride wherein the sodium hydride is present in a mole ratio of sodium hydride to triethoxysilane in a range between about 5:1 and about 1:10.

* * * * *